United States Patent

Knuth et al.

[11] Patent Number: 5,997,619
[45] Date of Patent: Dec. 7, 1999

[54] AIR PURIFICATION SYSTEM

[75] Inventors: Russell P. Knuth, Killingworth; William F. Carey, West Hartford, both of Conn.

[73] Assignee: NQ Environmental, Inc., Middletown, Conn.

[21] Appl. No.: 09/113,720

[22] Filed: Jul. 10, 1998

Related U.S. Application Data

[60] Provisional application No. 60/057,919, Sep. 4, 1997.

[51] Int. Cl.⁶ .............................. B01D 46/00; B03C 3/016
[52] U.S. Cl. ................................ 96/224; 55/356; 55/359; 55/385.2; 55/471; 55/472; 96/418
[58] Field of Search .............................. 96/224, 223, 418, 96/417; 55/467, 471, 472, 473, 356, 359, 383, 385.1, 385.2, 486, 487, DIG. 34

[56] References Cited

U.S. PATENT DOCUMENTS

| | | | |
|---|---|---|---|
| 2,478,393 | 8/1949 | Haarman | 34/80 |
| 2,553,711 | 5/1951 | Jackson | 96/224 |
| 2,709,954 | 6/1955 | Baker | 98/36 |
| 3,299,620 | 1/1967 | Hollingworth | 55/126 |
| 3,347,025 | 10/1967 | Wiley | 96/224 |
| 3,518,046 | 6/1970 | Cicirello | 21/53 |
| 3,576,593 | 4/1971 | Cicirello | 21/53 |
| 3,683,638 | 8/1972 | Devon | 62/264 |
| 3,757,495 | 9/1973 | Sievers | 96/224 |
| 3,804,942 | 4/1974 | Kato et al. | 96/224 |
| 3,812,370 | 5/1974 | LaViolette | 250/527 |
| 4,210,429 | 7/1980 | Golstein | 55/279 |
| 4,339,250 | 7/1982 | Thut | 55/383 |
| 4,370,155 | 1/1983 | Armbruster | 55/472 |
| 4,531,956 | 7/1985 | Howorth | 55/279 |
| 4,737,173 | 4/1988 | Kudirka et al. | 55/276 |
| 4,749,385 | 6/1988 | Brunner et al. | 55/97 |
| 4,750,917 | 6/1988 | Fujii | 96/224 |
| 4,787,922 | 11/1988 | Kulitz | 55/274 |
| 4,810,269 | 3/1989 | Stackhouse et al. | 55/356 |
| 4,900,344 | 2/1990 | Lansing | 55/322 |
| 4,909,815 | 3/1990 | Meyer | 55/316 |
| 4,959,010 | 9/1990 | Burtscher et al. | 431/12 |
| 5,069,691 | 12/1991 | Travis et al. | 55/126 |
| 5,129,928 | 7/1992 | Chan et al. | 55/385.1 |
| 5,185,015 | 2/1993 | Searle | 96/224 |
| 5,225,167 | 7/1993 | Wetzel | 422/121 |
| 5,240,478 | 8/1993 | Messina | 95/273 |
| 5,290,330 | 3/1994 | Tepper et al. | 55/356 |
| 5,399,319 | 3/1995 | Schoenberger et al. | 96/224 |
| 5,612,001 | 3/1997 | Matschke | 96/224 |
| 5,616,172 | 4/1997 | Tuckerman et al. | 96/16 |
| 5,656,242 | 8/1997 | Morrow et al. | 96/224 |

*Primary Examiner*—Duane S. Smith
*Attorney, Agent, or Firm*—Albert W. Hilburger

[57] ABSTRACT

A self contained air purification system includes an upright enclosed housing defining a germicidal chamber. A primary filter having a normally upstanding longitudinal axis has outer and inner peripheral surfaces, an interior plenum, and is supported on a base member. The housing has air inlets proximate the filter and air exhaust louvers in an upper member. Ultraviolet germicidal irradiation lamps are disposed in the germicidal chamber, and a resiliently mounted fan overlies the primary filter for drawing unclean air from the environment into and through the air inlets, through the primary filter, through the plenum and then into the germicidal chamber in a vortex-shaped whirling mass air stream flowing in a protracted course around and past the irradiation lamps for maximized exposure to the lamps, a purified air stream being discharged, after a final filtration, through the air exhaust louvers, then is returned to the environment. The primary filter includes an outermost particulate pre-filter for removal of particles of about 10 micron size and larger, an intermediate filter for removal of oxidizing gaseous pollutants, and an innermost filter being a HEPA filter for removal of about 99.6% of all particles of 0.3 micron size or larger. The irradiation lamps are aligned generally transverse to the air stream as it flows through the germicidal chamber and have sufficient intensity to destroy more than about 90% of airborne pathogenic particles which have not been entrained by the primary filter.

16 Claims, 5 Drawing Sheets

AIR PURIFICATION SYSTEM

This application claims the benefit of U.S. Provisional Application No. 60/057,919, filed Sep. 4, 1997.

BACKGROUND OF THE INVENTION

1. Field of the Invention

The present invention relates generally to a self-contained portable air movement and purification system, and more particularly, to such a system which is capable of removing particulate and bacterial contaminants and generally purifying the air of a contained environment.

2. Description of the Prior Art

A wide variety of air filter systems are presently available for use. These systems typically include a fan arrangement for circulating air, and a filter stage or perhaps multiple filter stages disposed in the air path so as to filter or otherwise purify air flowing therethrough. The air filters differ widely in their volume capacity, their efficiency of filtration, airflow directions, and their ease of portability.

Several different types of filtering stages are available for use in present day air filter systems. The air filter stage may have, for example, an electrostatic precipitator type of element which charges dust or other airborne contaminants and attracts the airborne contaminants to an electrically charged grid. In general, electrostatic air filter stages are expensive to fabricate and install, and they often require relatively costly maintenance. In addition, there is a substantial electrical power requirement over and above that needed for maintaining an air flow through the filter stage.

As another general type of air filtering, one or more layers of porous media alone are disposed in an air flow path for "mechanically" filtering or trapping airborne particles contained in the air flow. In general if a greater efficiency of filtering or germ or odor removal is desired, additional stages or filtering layers are added. This, however, multiplies the cost of the initial filtering stage and frequently results in a significant pressure drop across the filter, thus requiring a higher fan capacity with greater electrical consumption for maintaining a desired air flow.

Users of air filter systems are frequently concerned about the amount of air treated by a filter stage in a given time period, for example, requiring several changes of air volume in a room, for each hour of operation of the air filter system. This concept of room air filtering is frequently expressed as a number of "room air changes" per hour. For purposes of comparison, building codes frequently require that public restaurants and similar public buildings have at least one or two air changes per hour, meaning that a volume of air equal to that required to fill a room is completely removed and replaced by fresh air at least once or twice each hour that the room is open to the public. The present invention is particularly concerned with providing an air filter system capable of filtering the air in an entire room on the order of several times per hour.

In a practical air filter system, much more is needed than simply providing sufficient fan capacity to "turn over" the air filling a room at the desired rate. For example, the efficiency of the filter media, over its life span must be considered. As air is caused to flow through a porous filter media, airborne particles and the like are trapped in the filter media, thus reducing its porosity and increasing the resistance of the air flow through the filter stage.

Other types of air filtering media may be provided which react with dissolved chemicals suspended in the air. Such filters frequently operate by adsorbing the chemical contaminants by collecting those contaminants in condensed form on the media surface. The adsorbed contaminants have the potential for changing the surface properties of the air filter media and in particular, have the potential of changing the resistance to air flow through the media. While an air filter stage could be "oversized" so as to provide a minimal acceptable air conductance at the end of its useful life, the cost of the air filter media in the stage rises significantly as does the size of that filter stage.

In addition, special considerations must be given to particular types of air filter media. For example, activated charcoal is a popular type of air filter media in use today and is frequently utilized as a bed of charcoal particles through which an air flow is conducted.

Presently, there exists a need for a high volume portable room air filter unit having at least a minimum filtering efficiency for types of contaminants frequently encountered in everyday situations. Of particular interest is the availability of an effective portable air filter system for use in rooms frequented by the public, in smoke-filled offices, and especially in residences of people suffering from asthma or allergies. However, in order to be practical in use, the air filter system should be sufficiently small in size and readily portable so that it can be moved from room to room and so that it can also be easily moved within a room without significantly altering its operation or adversely affecting the comfort of occupants of the room. Several arrangements of portable room air filters have been proposed, yet the need for further improvements still exists.

Pollens, lung damaging dust, smoke, bacteria, viruses and any one of a number of other irritants and micro-organisms are quite likely in the air that everyone breathes. These irritants are carried by the wind, on people's clothing, on the hair or feathers of a pet, or sprayed about by a sneeze or a cough. Contact with these irritants is almost inevitable. Also, for persons plagued by the miseries of emphysema, asthma, hay fever or other allergies, contact with irritants and micro-organisms means unpleasant discomfort and usually sleepless nights. Although different types of air purifiers presently exist, they are not completely effective in removing these irritants and micro-organisms from the air. Further, existing air purifiers do not provide the combination of effective removal of these contaminants along with the provision of a germicidal chamber for killing bacteria and virus. Specific examples of the prior art relating to air movement and purification systems will now be considered.

U.S. Pat. No. 5,069,691 to Travis et al. discloses a portable vacuum and air filtration unit for cleaning heating, ventilation, and air conditioning ductwork in residential and commercial buildings. Filtered air is exhausted into the room in which the unit is located.

U.S. Pat. No. 4,900,344 to Lansing, U.S. Pat. No. 4,787,922 to Kulitz, U.S. Pat. No. 4,737,173 to Kudirka et al. and U.S. Pat. No. 4,531,956 to Howorth all disclose portable filtration devices for workplaces and the like. Howorth is of particular interest in providing a sterile air zone for surgery and surgical instruments. However, in each instance the devices are relatively short of stature and do not adequately provide separation of the clean exhaust air from the soiled intake air.

U.S. Pat. No. 4,749,385 to Brunner et al. discloses apparatus for providing clean and heated air simultaneously to a workplace such as on a production line for the manufacture of cathode ray tubes. Airflow is directed through a HEPA filter and an infrared heater and onto a panel assembly for the cathode ray tube. Ambient air is drawn into the apparatus through an annular intake surrounding a circular exhaust.

U.S. Pat. No. 4,909,815 to Meyer discloses mobile air cleaning apparatus especially suited for use in an automotive vehicle repair and/or assembly plant. Filtered air is directed downwardly over the surface of the vehicle, then captured at a location beneath the vehicle for return and additional filtration.

U.S. Pat. No. 3,299,620 to Hollingworth discloses apparatus for the treatment and purification of air which utilizes a liquid spray for cleansing the air of particulate matter.

U.S. Pat. No. 4,210,429 to Golstein et al. discloses an air purifier which incorporates a number of features improved over the earlier mentioned references including its relative height and the use of germicidal lamps. Nonetheless, the present invention is deemed to incorporate significant, patentable improvements thereon which will be related below.

A more recent development is disclosed in commonly assigned U.S. Pat. No. 5,616,172 to Tuckerman et al. which discloses a self contained air movement and purification system focused on infection control. The system of that invention comprises an elongated upright enclosed housing including a base module, side walks, and an upper module. A fan intermediate the base module and the upper module draws unclean air from a room containing the system through the base module, then discharges a purified air stream from the upper module. The base module includes a downward facing air intake opening spaced from the floor. A pair of pre-filters are disposed on the base module in stacked relationship for trapping relatively large particulate matter from the entering air stream. The upper module includes a discharge grille opening to the environment with angled louvers for guiding and re-directing the purified air stream from a HEPA-type filter into an inclined stream, flowing proximate to and along the ceiling of the room in which the system is located. A germicidal chamber intermediate the pre-filters and the fan contains a plurality of elongated and longitudinally extending ultraviolet germicidal irradiation lamps. Because of the remoteness of the upper module from the base module, undesirable mixing of unclean and purified air is minimized. In another embodiment, the discharge grille has a first opening with angled louvers as in the first embodiment and a second opening to which an attached conduit leads to an exterior region outside of the room to thereby create a negative pressure in the room in relation to the exterior region.

It was with knowledge of the foregoing state of the technology that the present invention has been conceived and is now reduced to practice. The actuation and deployment concept embodied by this invention is different from all of the devices reviewed above.

SUMMARY OF THE INVENTION

The present invention relates to a self contained air purification system which comprises an upright enclosed housing defining a germicidal chamber. An annular filter having a normally upstanding longitudinal axis has outer and inner peripheral surfaces, an interior plenum, and is supported on a base member. The housing has air inlets proximate the filter and air exhaust louvers in an upper member. Ultraviolet germicidal irradiation lamps are disposed in the germicidal chamber, and a resiliently mounted fan overlies the annular filter for drawing unclean air from the environment into and through the air inlets, through the annular filter, through the plenum and then into the germicidal chamber in a vortex-shaped whirling mass air stream flowing in a protracted course around and past the irradiation means for maximized exposure to said irradiation lamps, a purified air stream being discharged, after a final filtration, through the air exhaust louvers, then is returned to the environment. The annular filter includes an outermost particulate pre-filter for removal of particles of about 10 micron size and larger, an intermediate filter for removal of oxidizing gaseous pollutants, and an innermost filter being a HEPA filter for removal of about 99.6% of all particles of 0.3 micron size or larger. The irradiation lamps are aligned generally transverse to the air stream as it flows through the germicidal chamber and have sufficient intensity to destroy more than about 90% of airborne pathogenic particles which have not been entrained by the annular filter.

In one unit, the system of the invention is equipped with five-stage filtration, germicidal ultraviolet protection, and a powerful air flow system. At level one, a 10 micron, particulate pre-filter captures airborne particles like dust and pet dander. At the next level, a patented, specially blended carbon media comprising three materials, absorbs and oxidizes odors, gases, and chemicals. Together, these barriers complement the primary micro-filtration media of HEPA which traps particles including pollen, molds, dust, and bacteria down to 0.3 microns. Any bacteria that pass through the HEPA are then killed by the germicidal UV light. Finally, a carbon impregnated post filter reinforces the entire purification process.

As with any apparatus which must be engineered, there are design trade-offs which must be, and have been, considered. In regard to the present invention, there were four objectives deemed to be of primary importance for the air treatment system, specifically, infection control efficacy, safety, administrative control of the equipment, and the users' subjective requirements. These, in turn, translated into key factors of: (1) airflow, (2) noise, (3) filtration/germicidal action, and (4) safety features:

(1) the airflow needs to be maximized within the constraints of noise, germicidal action and safety. Because the general infection control mechanism is to dilute the contaminated air with clean, safe air (up to 100% dilution) the more air that can be processed, the faster and more complete the dilution will be;

(2) noise is a large user constraint: the higher the noise level of the equipment, the more objectionable it is to the people using the device. Noise originates with both the motor and the airflow. The higher the airflow, the noisier the unit will be and the more resistance in the air flow, the noisier the motor will be. The type of motor and fan blade design also influence the noise of the unit;

(3) germicidal action is also influenced by the airflow through the unit. The faster the transit time of the air through the unit, the less the cumulative dosage imparted by the ultraviolet lamps (UVGI—UltraViolet Germicidal Irradiation), and the less effective the UVGI is in killing the microbes. The use of a HEPA (High Efficiency Particulate Air) filter will also increase resistance to airflow as the velocity of the air increases. An upper limit occurs when it begins to self-destruct. The higher the airflow capacity of the HEPA filter, the more expensive it becomes. The invention has been designed to operate well within the rated capacity of the filters employed; and (4) safety features from both an operation and performance perspective include the capability of the system being operated by a broad range of users; ease of mobility of the system; readily available information concerning the condition and functioning of the active components of the system. Also, the combination of the UVGI lamps and the HEPA filter in series protects from purification failure; in this regard, it is noteworthy that any failure in purification makes this kind of machine an infection spreading rather than infection control device.

With the foregoing considerations in mind, important decisions have been made which have resulted in an air treatment system believed to be far superior to any personal-use air purification system currently available. To this end, the air filtration system of the invention comprises a metal housing with external holes for air flow into the unit sides and slots on the top for returning cleaned air outflow to the environment. The internal parts include a pre-filter, 15 pounds of oxidizing pellets, a round HEPA filter, a backward inclined fan with electric motor, a pair (or other suitable number) of 9 watt ultraviolet germicidal lamps, a ⅝" carbon pad holding one pound of pulverized carbon, variable speed control for the fan speed, and indicator lamps to monitor filter life and actual ultraviolet lamp function. Four small wheels on the bottom allow for easy mobility through the home or office.

This unit is specifically made for smaller rooms and residential or light commercial buildings intended to join in the marketplace the larger unit intended for use in doctors' offices and hospitals and disclosed in commonly assigned U.S. Pat. No. 5,616,172.

Important features of the present invention include:

- a housing which has been shortened and squared off, for example, to 14"×15" to better fit the decor of its intended use, namely, living rooms, bedrooms and offices;
- a revised fan mechanism changed to a backward inclined blade instead of a forward curved so as to eliminate any motor overloading if fan is operated without filters or with plugged filters;
- redirected airflow into the unit, changed from bottom most (underneath) to the sides so that extra dust loading will be visible in the new application, enabling a user to simply vacuum the sides so as to add life to both the pre-filters and the HEPA filter;
- a relocated germicidal chamber, moved to the discharge of the fan side so that the discharge air is disinfected by means of the UVGI irradiation instead of only the pre-filters. The new fan type and location also allows the fan shelf, fan motor, fan wheel, and leaving edges of the HEPA filter to be irradiated with direct and indirect light from the UVGI lamps;
- a post filter of carbon mesh has been added to adsorb any residual odors from the unit as well as any minute ozone ($O_3$) that may be produced by the fan motor of the UVGI lamps;
- a cavity has been added immediately upstream of the HEPA filter filled with a special formulation of particularly effective odor adsorbing and gas oxidization pellets.
- the top discharge vent system has been designed to provide sufficient air velocity for the discharge air to reach the ceiling and create the best airflow patterns. This type of flow has been researched by ASHRAE (American Society of Heating, Refrigeration and Air Conditioning Engineers) to create the most desirable mixing of air in a room
- top discharge cover is disposed at a 15 degree angle to aid in achieving the most effective airflow pattern and to assure that items such as drinking cups or cans, plants, papers and books cannot be placed on the top over the air discharge slots to thereby undesirably interfere with the clean air discharge from the unit.

The air purification system of the invention is portable and extremely easy to use. All that an operator need do is to wheel it into a room and plug it into an electrical receptacle. The operator can benefit from clean, purified air immediately. Further, the unit of the invention is designed to set up the correct air patterns, and is often most effective placed against a wall opposite the area needing the most cleaning.

The clean, purified air will be directed across the ceiling, and drop down around the total room area, pushing any dust, pollen or odors toward the floor and back into the unit. While the unit of the invention is effective wherever it is placed within the room, its placement is recommended at a wall opposite the region in which the clean air benefits are most desired.

Industry guidelines suggest at least six air changes per hour (ACH) for adequate airborne cleaning and allergy control. The system of the invention will change 21,000 cubic feet per hour (CFH) at high speed.

The upward air discharge provided by the system of the invention more completely mixes the air in a room by using the ceiling and upper spaces of the room to completely distribute the air to all areas. When air flow patterns move across the ceiling and upper spaces there is no furniture to short circuit the air back to the filter unit. When there is no short circuiting of the air, the mixing of all the air is more complete and therefore the filter unit is twice as effective with less drafts, than all the side, bottom or front air discharge type units, on the market today. This top discharge allows higher air flow rates to better clean the air rapidly with complete mixing, resulting in cleaner and purer air to breathe throughout the room. Used in rooms from 150 to 1500 square feet with twice the total room cleaning power than any other filter on the market today.

The Center for Disease Control documents that a filter with air flow patterns and air volume rates equal to the system of the invention will clean an average bedroom to 99 percent clean in 14 minutes.

A primary feature, then, of the present invention is the provision of a self-contained portable air movement and purification system.

Another feature of the present invention is the provision of such a system which is capable of removing particulate and bacterial contaminants and generally purifying the air of a contained environment.

Still another feature of the present invention is the provision of such a unit specifically intended for smaller rooms and residential or light commercial buildings.

Yet another feature of the present invention is the provision of such a system equipped with five-stage filtration, germicidal ultraviolet protection, and a powerful air flow capability.

Still a further feature of the present invention is the provision of such an improved air purifier that has an improved filtration efficiency capable of removing from the air particles down to about 0.3 microns in size with an efficiency of 99.97%.

Yet a further feature of the invention is to provide such a system which provides maximum separation between intake and exhaust regions to prevent short circuiting of the clean and unclean air streams.

Another feature of the invention is to provide such a system which provides for exhausting the clean air in an inclined stream, causing the purified air stream to flow proximate to and along the ceiling of the room in which the system is located.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
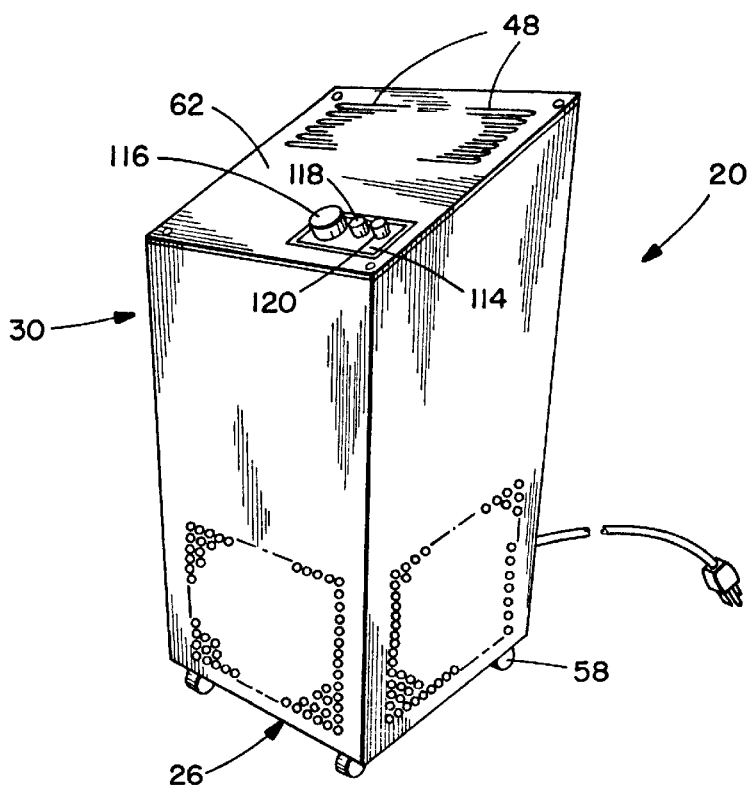
FIG. 1 is a perspective view of an air moving and purification system embodying the present invention.
Figure 2:
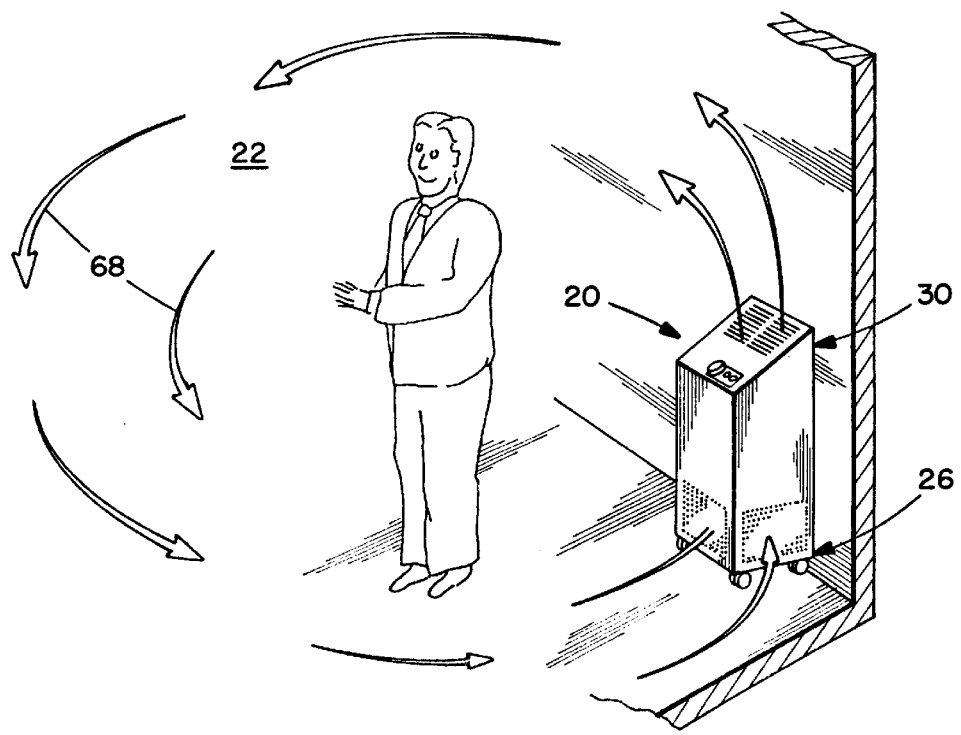
FIG. 2 is a perspective view illustrating the operation of the air moving and purification system illustrated in FIG. 1.

Turn now to the drawings and, initially, to FIGS. 1 and 2 which generally illustrate a self contained air movement system 20 for air purification and/or infection control of a local environment 22 such as the room of a home or office. As seen in greater detail in FIGS. 3 and 4, the system 20 comprises an elongated upright enclosed housing 24 including a base member 26, side walls 28, and an upper member 30 (FIG. 5) through which an air stream 32 may be caused to flow sequentially. The base member 26 is remote from the upper member and the housing 24 defines a germicidal chamber 33 intermediate the base member and upper member.

Figure 6:
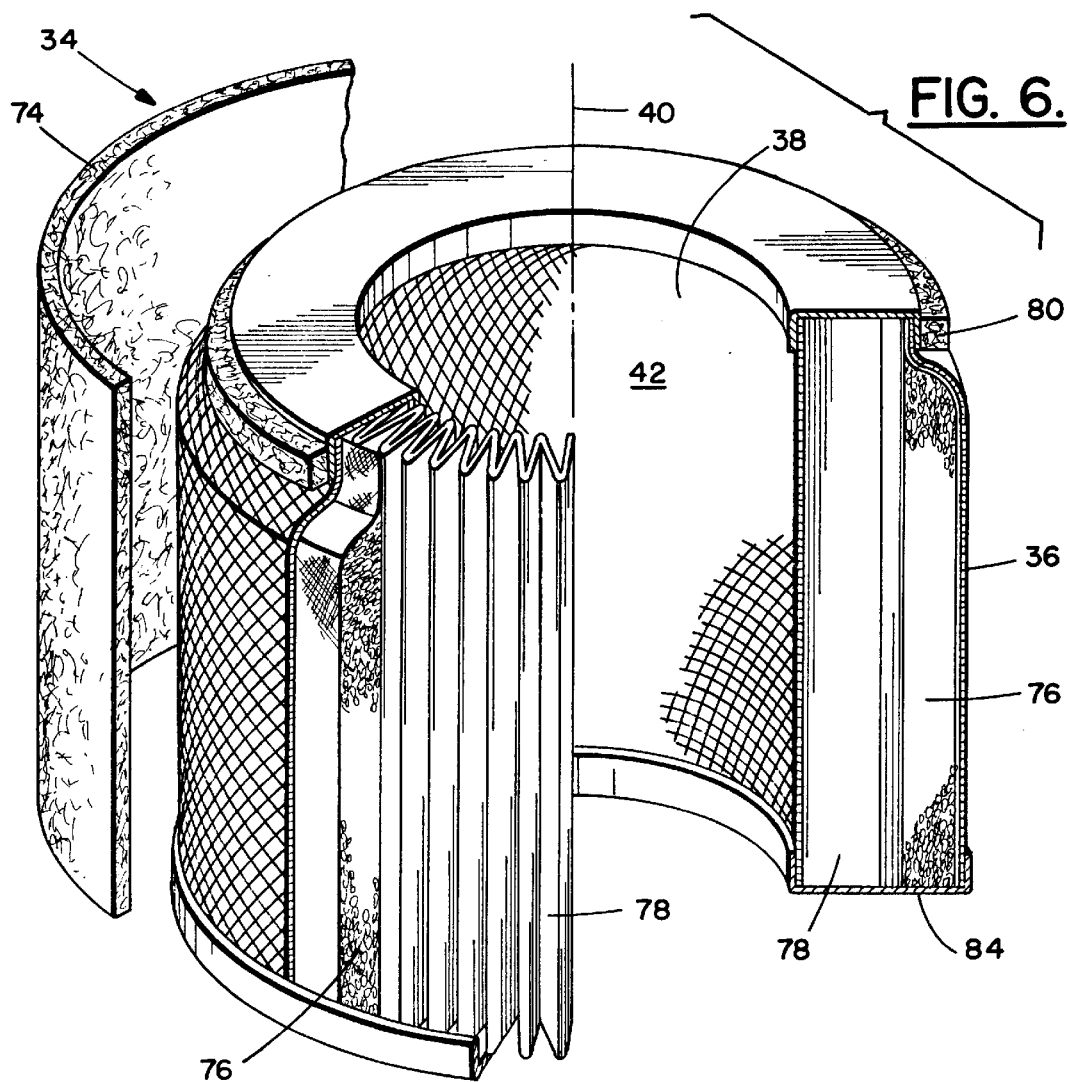
FIG. 6 is a detail exploded perspective view of a primary filter utilized by the air moving and purification system of the invention.
Figure 7:
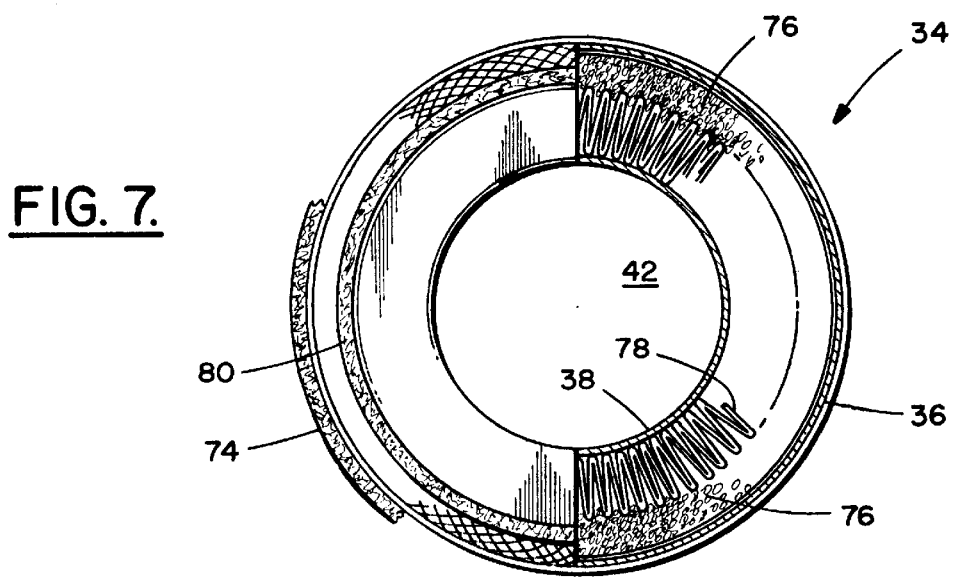
FIG. 7 is a detail cross section view of the primary filter illustrated in FIG. 6.

A primary filter member 34 which is of annular shape positioned around a normally upstanding longitudinal axis 40 (FIG. 6) has an outer peripheral surface 36, an inner peripheral surface 38, and defines an interior plenum 42 (FIG. 7). The inner peripheral surface 38 is spaced from the outer peripheral surface 36 and the primary filter member is mounted proximate, actually on, the base member. The primary filter member 34, which is replaceable, is suitably attached to the base member 26 as by fasteners 44 (FIG. 4) once properly located within the interior of the housing 28.

The housing 28 is suitably perforated so as to have numerous air inlets 46 proximate the primary filter 34 and air exhaust louvers 48 are provided in the upper member 30. In actual fact, the air inlets 46 are so located in the side walls 28 as to be generally coextensive with the outer peripheral surface 36 of the primary filter 34.

Ultraviolet germicidal irradiation lamps 50 are disposed in the germicidal chamber 33. They may be, for example, two nine watt lamps capable of producing the germicidal irradiation which is used in many hospital operating rooms world wide, to kill germs, yeast's and bacteria. Total irradiation power is strong enough to kill: viruses like: $E.\ coli$, Infectious Hepatitis, Influenza, and the like, and bacteria like: TB, Proteus Vulgaris, Salmonella Species, Typhoid Fever, Cholera, various Streptococcus and Staphylococus, Legionnaire's Disease, Infectious Jaundice. Eberthella Typhosa, Dysentery Bacilli, Diphtheria, Bacillus Anthracis, and the like.

A fan subsystem 52 beneath the ultraviolet lamps 50 overlies the primary filter 34 for drawing unclean air from the environment 22 (FIG. 2) into and through the air inlets 46, through the primary filter 34, through the plenum 42 and then into the germicidal chamber 33 in a vortex-shaped whirling mass air stream defined by arrows 54 (FIGS. 3, 4, and 5) flowing in a protracted course around and past the ultraviolet germicidal irradiation lamps 50 for maximized exposure to their output. This results in the discharge through the air exhaust louvers 48 of a purified air stream 32 for return to the environment.

Figure 4:
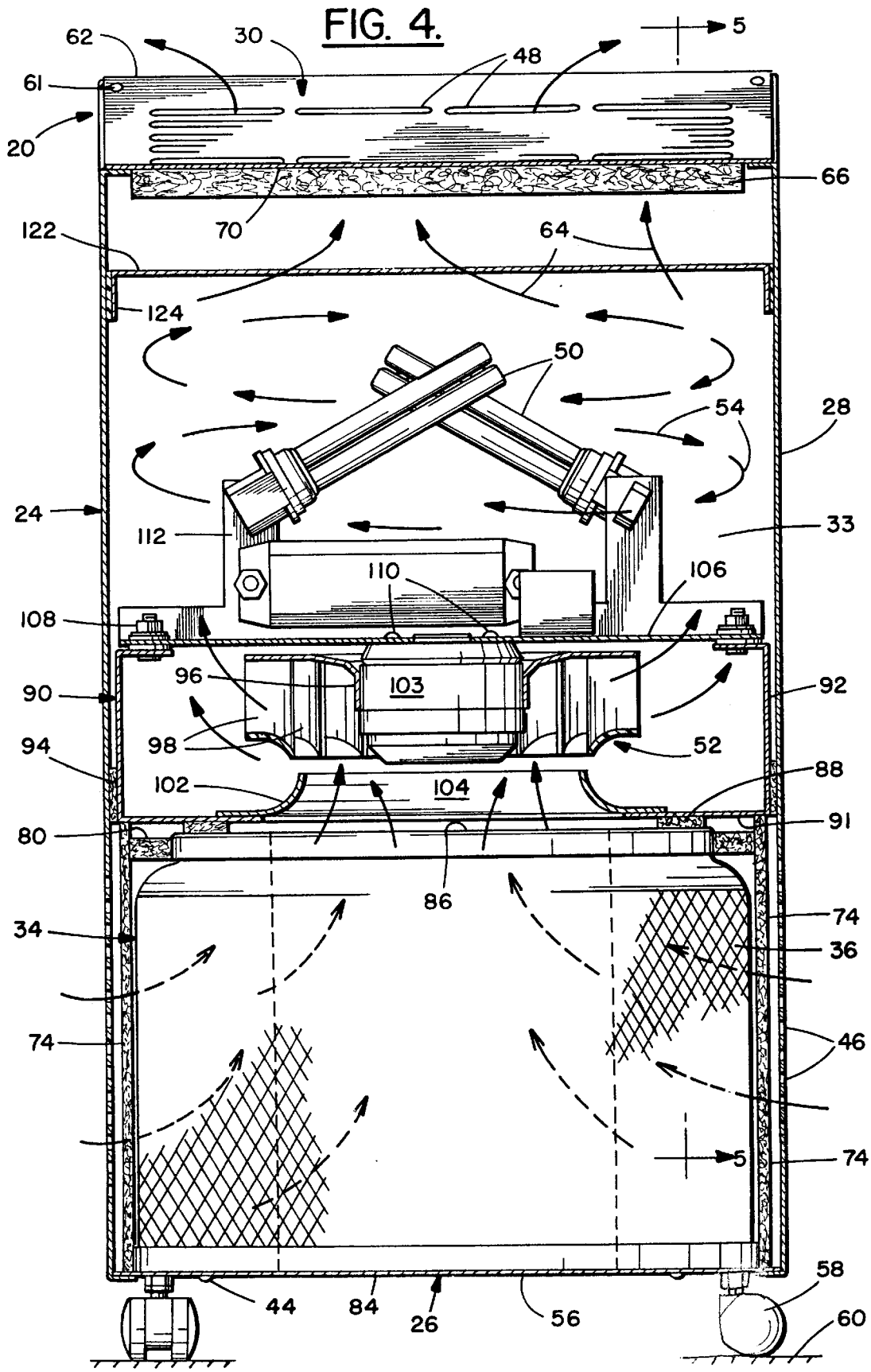
FIG. 4 is a front elevation view, in section, of the air moving and purification system illustrated in FIG. 3.
Figure 5:
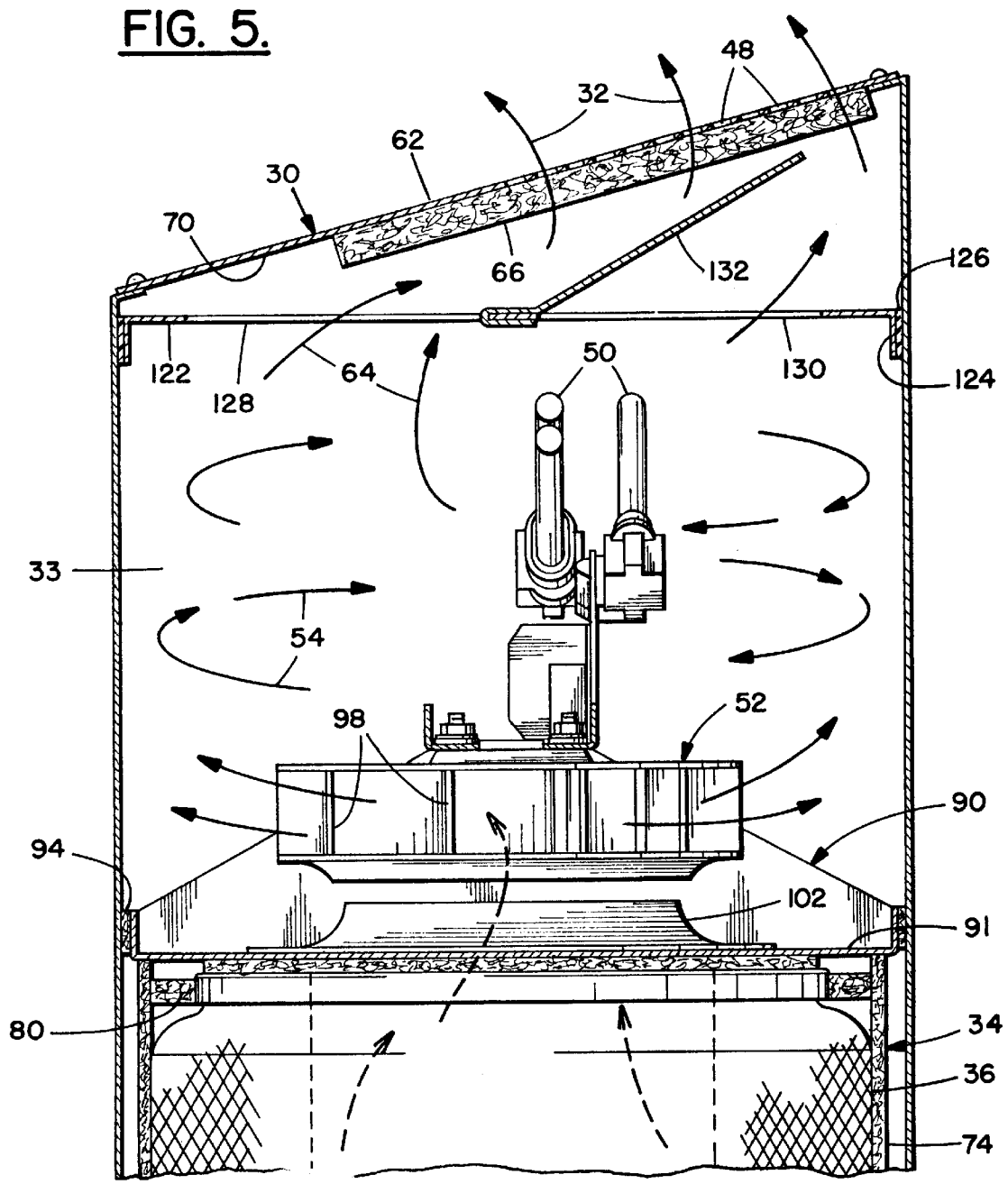
FIG. 5 is a cross section view, taken generally along line 5—5 in FIG. 4.

The base member 26 includes a base platform 56 integral with the side walls 28, being attached by means of rivets or other suitable fastener devices, and a plurality of spaced apart wheels 58 mounted on the base platform for rolling engagement with an underlying surface 60 (FIG. 4). Preferably, each of the wheels is rotatable about an axis parallel to a plane of the underlying surface and is also free to pivot about an upright axis.

The upper member 30 is selectively removable, as by withdrawal of fasteners 61, from the housing 28 to enable an operator to gain access to the germicidal chamber 33 so as to, for example, replace an expired UV lamp 50. It includes a discharge grille 62 defining a plurality of the air exhaust louvers 48 for communication between the germicidal chamber 33 and the environment 22. Preferably, the discharge grille 62 is angled, for example, 15° from the horizontal, for guiding and re-directing the purified air stream 64 from the germicidal chamber 33 into the inclined air stream 32 through the air exhaust louvers after exiting a downstream filter 66.

This results in the purified air stream flow, as illustrated by arrows 68 in FIG. 2 proximate to and along the ceiling (not illustrated) of the room in which the air movement and purification system 20 is located. Because of the remoteness of the upper member 30 from the base member 26, undesirable mixing of unclean and purified air is minimized. The angled surface of the discharge grill 62 also prevents the undesirable placement thereon of a variety of items such as drink containers, which otherwise could spill their contents into the air exhaust louvers 48 and harm the cleaning ability of the system 20, and plants, papers or books which otherwise could overlie the air exhaust louvers and interfere with or prevent the clean air discharge from the system.

The downstream filter 66, preferably a carbon mesh filter provided to adsorb any residual odors from the unit as well as any minute ozone ($O_3$) that may be produced by the fan motor 103 or the UVGI lamps 50, underlies the discharge grille 62 so as to be substantially coextensive with the air exhaust louvers 48. The discharge grille has an under surface which faces the germicidal chamber 33 and a suitable adhesive 70 is employed to bond the filter 66 to that under surface.

The primary filter 34 is of a layered, concentric, construction which includes:

an outermost particulate pre-filter 74, about one-half inch thick, for removal from the incoming air stream of particles of about 10 micron size and larger;

an intermediate carbon filter 76 for removal from the incoming air stream of oxidizing gaseous pollutants; this may be, for example, 15 pounds of specially formulated indoor air quality (IAQ) carbon adsorption granules as a second adsorptive media with 2 pounds of pulverized activated carbon post filter media; this combination has 3,290,000 square feet of total adsorptive surface area (80% more than other commonly-used materials) for the best gas and chemical removal commercially available today; the main adsorptive power comes from a granule specially designed to oxidize gaseous pollutants such as: hydrogen sulfide, sulfur dioxide, formaldehyde, ethylene, mercaptans, various aldehydes, and alcohols. This formulation provides 50% more active ingredients and reagents without the dust of other known products, therefore cleaning the air of gaseous pollutants while also not adding dust and small breathable particles to the air; also, this formulation has 20% greater density and absorptive capability than other known compounds or treated carbons; an example of a filter of this type which is suitable for purposes of the invention is Model No. ZK6 available from Cameron Carbon, Inc. of Chicago, Ill.;

an innermost filter 78 being a HEPA (high efficiency particulate air) filter for removal from the incoming air stream of approximately 99.6% of all particles of 0.3 micron size or larger; for purposes of explanation, a human hair is about 300 times too large to penetrate a HEPA filter; by way of example, a 14 inch diameter cylinder has 260 pleats of HEPA media and 11,520 square inches of total filter surface area.

As seen particularly well in FIGS. 6 and 7, the outermost filter 74, intermediate filter 76, and innermost filter 78 are all coaxial, coterminous and intimately disposed. The outermost filter or pre-filter 74 protects the media of the innermost HEPA filter 78 from becoming clogged with large particles which will shorten its overall life. The pre-filter 74 is preferably made of a spun poly pad which is easily removable washed and or replaced, for continued long life of the more expensive HEPA and carbon filters. This pre-filter can be washed or vacuumed to extend its service life. Foam sealing gasket 80 surrounding the upper region of the primary filter 34 assures that the air flow is through the primary filter 34 and does not leak out around the edges. Such leakage or bypass of unclean air typically reduces the overall effectiveness of many known systems.

The primary filter 34 has a lower end surface 84 mounted on the base member 26 and an upper end surface 86 parallel with and spaced from the lower end surface. The system further includes a resilient gasket 88 mounted on the upper end surface 86. In turn, a fan platform 90 is supported on the gasket 88 so as to overlie and be spaced from the upper end surface 86. The fan platform 90 includes an underlying base plate 91 which extends laterally of a longitudinal axis of the housing 24 to opposite upstanding ends 92 which are spaced, respectively from the opposed side walls 28. Again, a resilient gasket 94 is interposed between each of the upstanding ends 92 and an associated one of the side walls 28.

Figure 8:
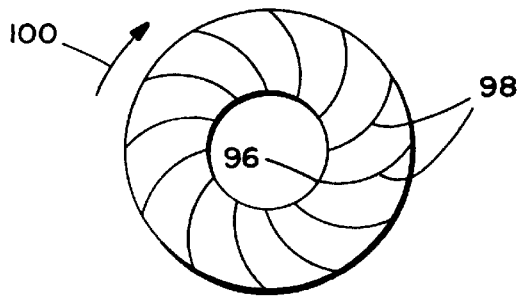
FIG. 8 is a diagrammatic illustration of an impeller blade construction utilized by the fan subsystem of the invention.

In a manner now to be described, the fan subsystem 52 is mounted on the fan platform 90 intermediate the opposite upstanding ends 92. The fan subsystem includes a hub 96 (FIG. 4) and a plurality of impeller blades 98 fixed to and extending radially from the hub. As seen especially well in FIG. 8, the impeller blades 98 are inclined opposite to the direction of fan rotation as indicated by an arrow 100. This is a preferable construction which results in higher tip speeds and provides high fan efficiency and relatively low noise levels with "non-overloading" horsepower characteristics. In a non-overloading fan, the maximum horsepower occurs near the optimum operating point so that any variation from that point due to a change in system resistance results in a reduction in operating horsepower. A fan motor 103, preferably a variable speed unit, is employed for rotating the hub 96 about a rotational axis generally aligned with the longitudinal axis of the primary filter 34.

Figure 3:
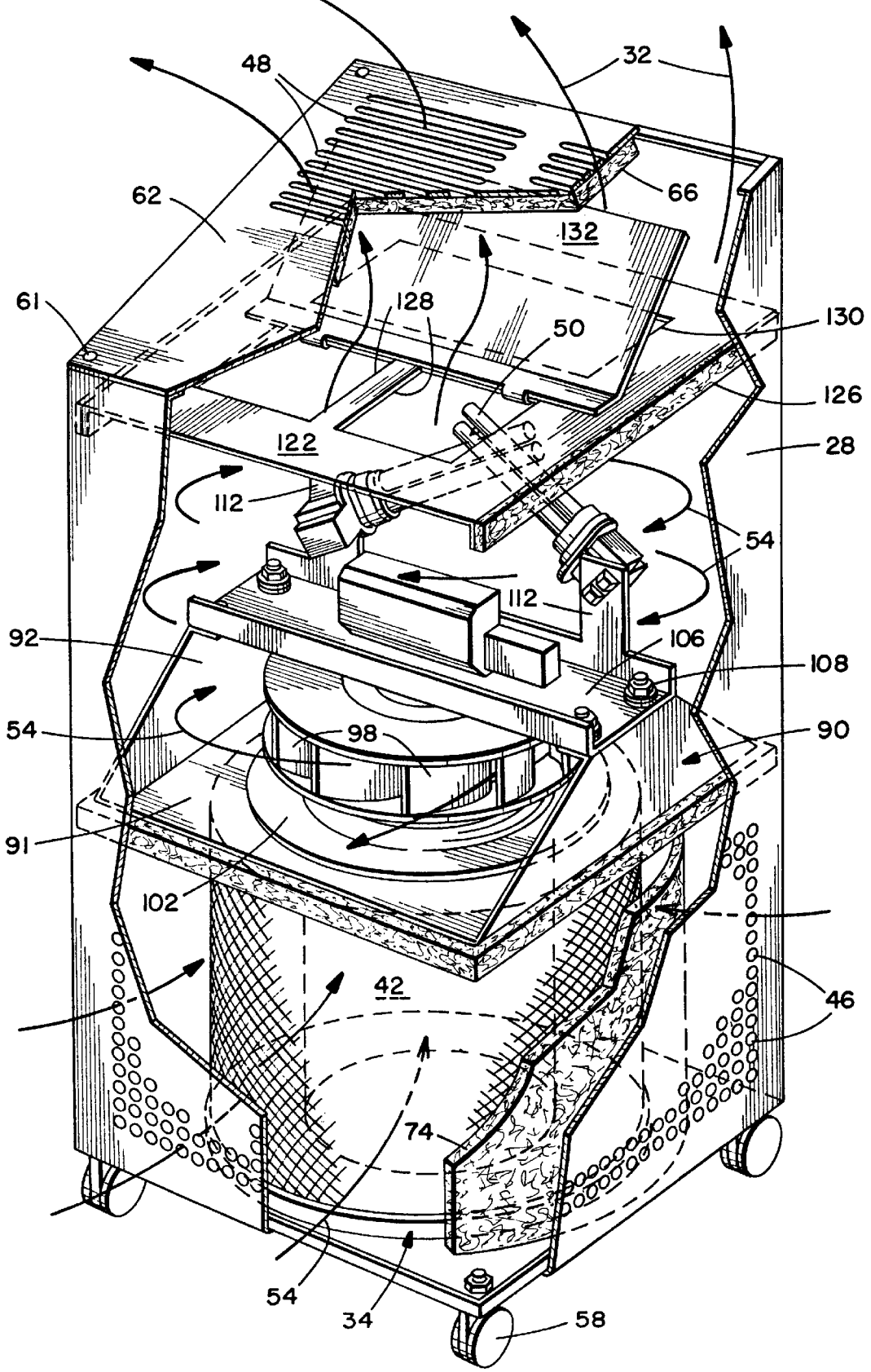
FIG. 3 is a perspective view of the air moving and purification system of the invention, partially cut away and in section for clarity.

The fan platform 90 also includes a circular upstanding collar on the base plate 91 defining a central air passage 104 for delivering air from the interior plenum 42 of the primary filter 34 to the fan subsystem 52. An elongated fan mounting plate 106 extends between opposite ends mounted, respectively, to the upstanding ends 92 of the fan platform 90 as with suitable fasteners 108 (FIGS. 3 and 4). The fan motor 103 is mounted in a suspended fashion on the fan platform 90. Specifically, the fan motor 103 is mounted on the plate 106 as with fasteners 110 (FIG. 4) and depends therefrom intermediate the plate 106 and the base plate 91.

With this construction vibration and its accompanying noise is minimized and, as earlier mentioned, air flowing out of the primary filter 34 flows through the central air passage 104 defined by the circular upstanding collar 102, then through the impeller blades 98.

The fan mounting plate 106 may actually be channel-shaped and includes a pair of laterally spaced upstanding finger support members 112. Suitable mounting devices are provided for mounting the ultraviolet lamps 50 on each of the upstanding finger support members so as to be aligned generally transverse to the air stream flowing through the germicidal chamber 33. The ultraviolet lamps 50, which are preferably of a specific type (253.7 nm wavelength) known to kill germs contained in the tiny airborne droplets (droplet nuclei) that transmit some infection (measles, tuberculosis, influenza) from person to person within buildings, have sufficient intensity to destroy more than about 90% of airborne pathogenic particles which have not been entrained by the primary filter 34.

An operating panel 114 is desirably provided for the system 20, preferably on the discharge grille 62 of the upper member 30. Typically, the operating panel may include a speed control knob 116 for controlling the speed of the fan motor 103 and indicators for indicating the condition of operation of the ultraviolet lamps and of the primary filter. Specifically, the indicators include a normally unlighted red indicator lamp 118 which, when lighted, indicates that the primary filter 34 requires replacement and a normally lighted green indicator lamp 120 which, when unlighted, indicates that one or the other of the ultraviolet lamps requires replacement.

A particularly beneficial feature of the invention resides in the five stage filtration provided by the system 20. At level one, a 10 micron, particulate pre-filter 74 captures airborne particles like dust and pet dander. At the next level, specially blended carbon media utilizing three materials, absorbs and oxidizes odors, gases, and chemicals. Together, these barriers complement the microfiltration HEPA media of the primary filter 34 which traps particles including pollen, molds, dust, and bacteria down to 0.3 microns. Any bacteria that pass through the HEPA are then killed by the germicidal UV lamps 50. Finally, a carbon impregnated post, or downstream, filter 66 reinforces the entire purification process.

Furthermore, the design of the system takes into account the fact that the air flow pattern into a fan must be smooth and of equal pressure across the inlet area so that the efficiency of the fan is at its optimum, also so that the exiting air is evenly spaced around the outlet from the fan. With the radial or annular design of the primary filter 34, the airflow through the filter passes into the inside, or interior plenum 42 from all regions around the outer periphery of the filter. This air then proceeds up through the interior plenum and the central air passage 104 directly beneath the fan inlet as determined by the upstanding collar 102. This air then enters the fan and is forced out symmetrically around the circumference of the impeller blades 98. The air exits symmetrically because it enters symmetrically. The exiting air flow needs to be as symmetrical as possible so that the air flow pattern in the germicidal chamber 33 above the fan subsystem 52 acts on the germs in this airflow, equally, throughout the chamber.

Thus, the air proceeds vertically through the primary filter 34 into the fan subsystem 52 and, with the impeller blades 98 pulling the air along, their circular motion transfers the air stream direction from vertical to horizontal. This motion also imparts a tangential and circular component to the air stream, similar to that of a circular lawn water sprinkler. The air flow then continues out of the fan subsystem radially and continues up along the side walls 28 of the housing 24. This radial motion re-routes the air flow so that the distance actually traveled by the air stream to the top of the unit is substantially lengthened. The resulting helical path thereby traveled by the air stream may be four times the straight line distance from the fan subsystem 52 to the air exhaust louvers 48 and this extra distance thereby increases the germ-killing residence time of the air being purified in the vicinity of the ultraviolet lamp 50.

Just beneath the discharge grille 62 of the upper member 30 is a top shelf 122 which overlies the irradiation lamps 50. The top shelf extends between opposing side walls 28 of the housing 24 and includes downturned flanges 124 which are mounted to the side walls as by double-sided adhesive tape 126, or in some other manner. The top shelf 122 serves to improve the rigidity of the housing 24 and also to protect the components in the interior of the housing. Openings 128, 130 are provided in the top shelf to provide access to the interior of the housing for purposes such as the removal and replacement of spent lamps 50. Suitably mounted to the top shelf and extending upwardly and angularly disposed relative to the top shelf is a baffle plate 132, preferably with a reflective interior surface which serves to return radiation from the lamps 50 to the germicidal chamber 33 and prevent its escape.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A self contained air movement system for at least one of air purification and infection control comprising:
    an elongated upright enclosed housing including a base member, side walls, and an upper member through which an air stream may be caused to flow sequentially, said base member being remote from said upper member, said housing defining a germicidal chamber therein;
    primary filter means having an outer peripheral surface, an inner peripheral surface, and defining an interior plenum, said inner peripheral surface being spaced from said outer peripheral surface, said primary filter means being mounted proximate said base member;
    said housing having air inlet means proximate said primary filter means and having air exhaust means in said upper member;
    ultraviolet germicidal irradiation means disposed in the germicidal chamber; and
    fan means overlying said primary filter means for drawing unclean air from the environment into and through the air inlet means, through said primary filter means, through the plenum and then into the germicidal chamber in a vortex-shaped whirling mass air stream flowing in a protracted course around and past said irradiation means for maximized exposure to said irradiation means whereby a purified air stream is discharged through the air exhaust means in said upper member for return to the environment.

2. A self contained air movement system as set forth in claim 1
    wherein said primary filter means includes an annular filter device having a normally upstanding longitudinal axis.

3. A self contained air movement system as set forth in claim 1
    wherein said primary filter means is mounted on said base member; and
    wherein the air inlet means are located in said side walls generally coextensive with said outer peripheral surface of said primary filter means.

4. A self contained air movement system as set forth in claim 1
    wherein said base member includes a platform integral with said side walls and wheel means mounted on said platform for rolling engagement with an underlying surface, said filter means being supported on said base member.

5. An air movement system as set forth in claim 4
    wherein said wheel means include a plurality of spaced apart wheels, each of which is rotatable about an axis parallel to a plane of the underlying surface and also free to pivot about an upright axis.

6. A self contained air movement system as set forth in claim
    wherein said upper member includes:
        a discharge grille defining louver means for communication between said germicidal chamber and the environment; and
        downstream filter means underlying said discharge grille;
        said discharge grille being angled for guiding and re-directing the purified air stream from said germicidal chamber into an inclined air stream through said louver means, after exiting said downstream filtration means, causing the purified air stream to flow proximate to and along the ceiling of the room in which said air movement and purification system is located and, because of the remoteness of said upper member from said base member, minimizing undesirable mixing of unclean and purified air.

7. A self contained air movement system as set forth in claim 6
    wherein said discharge grille has an under surface facing the germicidal chamber; and
    wherein said downstream filter means includes:

a carbon mesh discharge filter substantially coextensive with said louver means; and adhesive means bonding said discharge filter to said under surface.

8. An air movement system as set forth in claim 1 wherein said ultraviolet germicidal irradiation means includes a plurality of ultraviolet lamps aligned generally transverse to the air stream flowing through the germicidal chamber and having sufficient intensity to destroy more than about 90% of airborne pathogenic particles which have not been entrained by said primary filter means.

9. An air movement system as set forth in claim 1 including:

indicator means outside of said housing for indicating the condition of operation of said ultraviolet germicidal irradiation means and said primary filter means.

10. An air movement system as set forth in claim 9 including:

wherein said indicator means includes:
a normally unlighted indicator lamp which, when lighted, indicates that said primary filter means requires replacement; and
a normally lighted indicator lamp which, when unlighted, indicates that said irradiation means requires replacement.

11. An air movement system as set forth in claim 1 including:

wherein said fan means includes:
a variable speed fan; and
a speed control knob on the outside of said housing for controlling the speed of said fan.

12. An air movement system as set forth in claim 2 wherein said primary filter means includes:

an outermost particulate pre-filter for removal from the incoming air stream of particles of about 10 micron size and larger;
an intermediate filter for removal from the incoming air stream of oxidizing gaseous pollutants; and
an innermost filter being a HEPA filter for removal from the incoming air stream of approximately 99.6% of all particles of 0.3 micron size or larger;
said outermost filter, said intermediate filter, and said innermost filters all being coaxial, coterminous and intimately disposed.

13. An air movement system as set forth in claim 1 wherein said primary filter means has a lower end surface mounted on said base member and an upper end surface parallel with and spaced from said lower end surface; and including:

resilient gasket means mounted on said upper end surface; and
a fan platform mounted on said gasket means so as to overlie and be spaced from said upper end surface, said fan platform extending laterally of a longitudinal axis of said housing to opposite upstanding ends thereof spaced, respectively from an opposed pair of said side walls; and
resilient gasket means between each of said upstanding ends and an associated one of said side walls;
said fan means being mounted on said fan platform intermediate said opposite upstanding ends.

14. An air movement system as set forth in claim 13 wherein said fan means includes;

a hub;
a plurality of impeller blades fixed to and extending radially from said hub, said impeller blades being inclined opposite to the direction of fan rotation; and
a fan motor for rotating said hub about a rotational axis generally aligned with the longitudinal axis of said primary filter means.

15. An air movement system as set forth in claim 13 wherein said fan platform includes:

a circular upstanding collar defining a central air passage; and
an elongated fan mounting plate extending between opposite ends mounted, respectively, to said upstanding ends of said fan platform, said fan motor being mounted on said fan platform so as to be suspended therefrom;
whereby air flowing out of said primary filter means flows through the central air passage defined by said circular upstanding collar, then through said impeller blades.

16. An air movement system as set forth in claim 15 wherein said fan mounting plate includes:

a pair of laterally spaced upstanding finger support members;
wherein said ultraviolet germicidal irradiation means includes a plurality of ultraviolet lamps aligned generally transverse to the air stream flowing through the germicidal chamber and having sufficient intensity to destroy more than about 90% of airborne pathogenic particles which have not been entrained by said primary filter means; and including:
means for mounting an ultraviolet lamp on each of said upstanding fingers.

\* \* \* \* \*